(12) United States Patent
Besson

(10) Patent No.: US 7,781,614 B2
(45) Date of Patent: Aug. 24, 2010

(54) METHOD FOR TREATING AN IMIDE ORGANIC SOLUTION BEARING A SULPHONYL GROUP

(75) Inventor: Bernard Besson, Les Echets (FR)

(73) Assignee: Rhodia Chimie, Aubervilliers (FR)

( * ) Notice: Subject to any disclaimer, the term of this patent is extended or adjusted under 35 U.S.C. 154(b) by 800 days.

(21) Appl. No.: 10/505,043

(22) PCT Filed: Feb. 14, 2003

(86) PCT No.: PCT/FR03/00482

§ 371 (c)(1),
(2), (4) Date: Apr. 27, 2005

(87) PCT Pub. No.: WO03/070694

PCT Pub. Date: Aug. 28, 2003

(65) Prior Publication Data

US 2005/0222460 A1   Oct. 6, 2005

(30) Foreign Application Priority Data

Feb. 20, 2002   (FR) .................................. 02 02137

(51) Int. Cl.
*C07C 213/00* (2006.01)
(52) U.S. Cl. .................... 564/281; 564/114; 564/80; 564/82; 564/291; 564/296
(58) Field of Classification Search ............. 564/281, 564/291, 296, 80, 82, 114
See application file for complete search history.

(56) References Cited

U.S. PATENT DOCUMENTS 5,256,821 A * 10/1993 Armand ...................... 564/82
5,502,251 A * 3/1996 Pohmer et al. ................ 564/82

FOREIGN PATENT DOCUMENTS

EP   0 364 340   4/1990

OTHER PUBLICATIONS

Matsumoto et al, Highly conductive room temperature molten salts based on small trimethylalkylammonium cations and bis(trifluoromethylsulfonyl)imide Chemistry Letters, 2000, No. 8, pp. 922-923.*
Sheldon, R., Catalytic reactions in ionic liquids Chem.Commun., 2001, 2399-2407.*
Ault, A., Techniques and Experiments for Organic Chemistry, fifth ed., Waveland press, Inc., 1987, pp. 106-108.*
International Search Report dated Oct. 2, 2003 issued in PCT/FR2003/00482.
Wasserscheid et al., "Synthesis and Properties of Ionic Liquids Derived from the 'Chiral Pool'", Chemical Communications, No. 3, pp. 200-201, Jan. 7, 2002.

* cited by examiner

*Primary Examiner*—Peter G O'Sullivan
*Assistant Examiner*—Sudhakar Katakam
(74) *Attorney, Agent, or Firm*—Buchanan Ingersoll & Rooney PC

(57) ABSTRACT

The invention relates to a method of treating an impure organic composition of ammonium imide, one of the substituents of which imide ion is a sulfonyl carried by a perhalogenated, advantageously perfluorinated carbon, characterized in that said composition is subjected to a step of liquid-liquid extraction by means of an aqueous phase and containing, as impurity, at least one of the chemical species chosen from halides, sulfonates and sulfinates, in particular those whose sulfur is carried by a perhalogenated carbon.

12 Claims, No Drawings

METHOD FOR TREATING AN IMIDE ORGANIC SOLUTION BEARING A SULPHONYL GROUP

This application is an application under 35 U.S.C. Section 371 of International Application Number PCT/FR03/00482 filed on Feb. 14, 2003.

The subject of the present invention is a technique for purifying sulfonated imides from impure mixtures containing them. It relates more particularly to the purification of sulfonated imides in which the sulfur bearing the sulfonic functional group is attached to a perhalogenated, advantageously perfluorinated, atom. The imides carrying a sulfonic functional group, itself attached to a perhalogenated atom, although they have been known for ages, are currently developing rapidly. The reason for this is that these compounds are used as constituent elements of lithium salts found in high-performance batteries.

It should be recalled that imides are compounds having the functional group below:

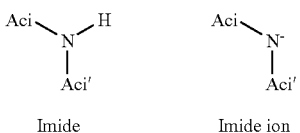

Imide      Imide ion

The imide ion functional group is only the deprotonated anionic form of the imide which has two substituents which are residues corresponding to oxygenated acids from which an OH group has been removed. The imides, or imide ions, covered by the present invention are those in which one of the Aci or Aci' groups is a sulfonyl group, advantageously both Aci and Aci' groups are sulfonyls. The sulfonyl functional group, or one of the sulfonyl functional groups when there are two of them, is carried by a perhalogenated, advantageously perfluorinated, carbon. More particularly covered are the imides containing a perhalogenated carbon on each of the substituents (here Aci and Aci'), said perhalogenated carbon being advantageously carried by an atom linked directly to the nitrogen.

These imide ions have in particular properties which have distinguished them as being value materials for the manufacture of batteries, which properties are, on the one hand, a very high acidity of the imide and, on the other hand, an absence of complexing power of the imide ion toward various cations.

These same properties make purification operations extremely difficult and delicate. The high acidity means a high dissociation and a high dissociation means a high solubility in polar media and in particular in water. In addition, these highly acidic compounds form, in general, addition compounds with water and it is often very difficult to separate these highly acidic compounds with water. The most common techniques for purifying these imides are techniques of recrystallization, in particular of recrystallization of their salts.

These imides are in general synthesized by the action of sulfonyl halides on trivalent nitrogen-containing derivatives carrying hydrogen (such as and in particular ammonia and amide) and in difficult cases, carrying a trialkylsilyl group. The sulfonyl group in general carries a perhalogenated carbon linked directly to the sulfur.

The sulfonyl halides currently most widely used are perfluoroalkanesulfonyl fluorides and chlorides and in particular $C_1$ and $C_2$ perfluoroalkanesulfonyl fluorides and chlorides.

Techniques for synthesizing this type of compounds are described in particular in patent applications by the company Central Glass and by the applicant.

The difficulty of this type of synthesis leads to the presence of impurities in significant quantities and in particular sulfonic and sulfinic acids corresponding to the sulfonyl acid chloride. There are also found as impurities the starting nitrogen-containing derivative and the amines which are often used for neutralizing the acids formed during the reaction, and the possible amines of a particular type which are used as catalysts.

Another source of these imides or of their salts, the imide ions, is the recycling of catalysts or of used batteries. There are found in these recycling products the same type of impurities as those which have just been described above, except maybe those derived from the amines used as catalysts (such as and in particular dialkylaminopyridines), it being possible for the other amines to be introduced in order to facilitate the separation and the recovery of the constituents of the batteries.

Moreover, liquid/liquid extraction techniques are in general hardly purifying, all these organic compounds are extracted in the organic phase; in addition, the compounds synthesized and/or the impurities and the starting compounds are amphiphilic, play the role of a third solvent and are even capable of having surfactant properties. The fatty amines are additionally known to be amphiphilic.

In addition, in order to be able to carry out, under good conditions, purifications by (liquid-liquid) extraction, it is necessary, on the one hand, for the partition coefficients between, on the one hand, the product(s) to be retained and, on the other hand, the impurities to be removed, to be very different and, on the other hand, for the partition coefficient of the impurity to be removed not to be too low in relation to the vector phase of said impurity.

In other words, if the organic phase $\phi_o$ is that from which it is desired to remove the compound(s) considered as impurity (impurities) and to keep the desired compounds and the aqueous phase $\phi_a$, the washing phase, then in order to avoid having excessive stream to handle, the partition coefficient of the impurity ($\phi_a/\phi_o$) considered, namely the ratio at equilibrium between the content of impurity per unit of quantity of material in the aqueous phase $\phi_a$ and the content of impurity per unit of quantity of material in the organic phase $\phi_o$, should be as high as possible and in any case at least equal to 1, advantageously to 2, preferably to 5. Of course, when the washing phase is the organic phase $\phi_o$, the condition to be observed is the opposite, namely that it is the partition coefficient ($\phi_o/\phi_a$) which should be high and at least equal to 1, advantageously to 2, preferably to 5.

It should finally be emphasized that the amphiphilic character of the acids containing polyfluorinated carbon(s) makes prediction of their behavior very difficult.

Accordingly, one of the aims of the present invention is to provide a method which allows recovery and enrichment of solutions containing the imides or imide ions referred to above.

Another aim of the present invention is to provide a method of the above type which makes it possible to separate the imides, or the imide ions, from the sulfonic acids corresponding to the constituent sulfonyl of at least one of the branches of the imide or imide ion functional group.

Another aim of the present invention is to provide a method of the above type which makes it possible to separate the imides or the imide ions from the acids, their sulfinic salts corresponding to the reduction of the constituent sulfonyl groups of one of the branches of the imide functional group.

Another aim of the present invention is to provide a technique which makes it possible to separate the imides or the imide ions from the various halides which may have been released, which may be present in the reaction mixture or recycling mixture. The halides most commonly released are fluoride ions and/or chloride ions.

These aims, and others which will subsequently emerge, are achieved by means of a method of treating an impure organic composition of ammonium imide, one of the substituents, advantageously both of the substituents, of which imide ion is a sulfonyl carried by a perhalogenated, advantageously perfluorinated carbon, characterized in that said composition is subjected to a step of liquid-liquid extraction by means of an aqueous phase and in that said impure organic composition contains, as impurities, at least one of the chemical species chosen from halides, sulfinates and sulfonates, in particular those whose sulfur is carried by a perhalogenated carbon.

It is appropriate to mention that previous trials dissuaded persons skilled in the art from using such techniques for carrying out extensive purification. Indeed, the partition coefficients obtained from the reaction mixture were not at all favorable. A plausible explanation is that there were too many organic compounds, in particular basic compounds (salified or not, especially in hydrohalide form), in the aqueous phase. Following studies carried out by the inventors, a surprising aspect of the invention is that the partition coefficients improve with the course of the extraction.

Also, when a reaction mixture is to be treated, the first biphasic liquid/liquid system is not according to the invention. To systematize and quantify this teaching, it is desirable to specify that it is advisable to ensure that the aqueous phase contains by mass at least ⅔, advantageously at least ¾, preferably at least 8/10, more preferably 9/10, of water. It is also preferable that the concentration of organic base, most often amines, in the aqueous phase is at most equal to 1 mol; advantageously 0.5; preferably 0.2; more preferably 0.1 mol per kg or per liter (in molality or in molarity: the difference is quite small).

The expression perhalogenated carbon should be understood to mean a carbon of $sp^3$ hybridization, bearing no hydrogen and containing, in addition to its linkage with the chalcogen (here sulfur), at most 2, advantageously at most 1, radicals, all the other atoms being halogens; said radicals are advantageously chosen from electron-attracting groups (that is to say whose Hammett constant $\sigma_p$ is greater than zero but they are advantageously such that this constant is at least equal to 0.15; preferably, to 0.2), especially when there are 2 thereof.

Thus, according to the present invention, a perhalogenated carbon advantageously carries at least two halogens, these two halogens being advantageously at least partially and, preferably totally, fluorine; in other words a perhalogenated carbon is advantageously a methylene carrying a fluorine and another halogen, which is advantageously fluorine.

An aqueous phase will be designated below by $\phi_a$ and an organic phase by $\phi_o$.

The present invention may be carried out with the aid of a method comprising several liquid-liquid extraction steps by means of an aqueous phase, but at least one of these steps should be carried out at a basic pH, that is to say that the pH after extraction remains greater than 7.

It is preferable that at least one of the liquid-liquid extractions is carried out such that the pH at the end of extraction (that is to say the pH of the aqueous phase on leaving the extraction after the final decantation) is at least equal to 9, advantageously to 10, preferably, in particular when there are relatively large proportions of perfluoroalkanesulfonic acids to be removed, at least equal to 11.5. The pH may be regulated by adding base initially before contact with the organic phase, such that the aqueous phase contains sufficient base to maintain the final pH at the preceding values. As will be recalled below, the quantity of base, as equivalent, to be used is advantageously at least the sum of the quantity of base necessary to bring the aqueous phase (considered alone) to the desired pH and of the quantity, as equivalent, of acid impurities salified with the organic base. This quantity is advantageously increased by a quantity ranging from 0 to 20% of the imide to be recovered, preferably from 1% to 10%, more preferably from 1 to 5%.

However, it is also possible to adjust the pH during contact so that it is always and especially in the end in the above region.

To obtain good results, it is preferable for said ammonium to have a number of carbons at least equal to 5, preferably at least equal to 6, more preferably at least equal to 7.

To obtain good results, it is preferable to avoid the number of carbons being too high, thus, it is preferable that the total number of carbons of said ammonium is at most equal to 12, advantageously to 10. According to the present invention, it is preferable that the ammonium carries at least two hydrocarbon-based chains (that is to say containing both carbon and hydrogen, attached to the nitrogen by a secondary carbon of $sp^3$ hybridization). It is also preferable that said ammonium is a protonated amine, said amine advantageously not being capable of being alkylated.

As examples of amines which are not capable of being alkylated, there may be mentioned tertiary amines advantageously containing, as substituent(s), at least one hydrocarbon radical attached to the nitrogen by a secondary carbon. As example of amines which give good results, there may be mentioned the diisopropylethylamine, often designated by its acronym (DiPEA). For it to be particularly advantageous to use the method according to the present invention, it is necessary that the impure organic composition of ammonium imide ion contains impurities chosen from sulfonates, in particular sulfonate ions in which the sulfur is carried by a perhalogenated carbon. It is also desirable that the sulfonate ion whose sulfur is carried by a perhalogenated carbons contain no more than 3, advantageously no more than 2 perfluorinated atoms per sulfonate functional group.

It is also desirable that said sulfonate ion, present as impurities, and having a sulfur carried by a perhalogenated carbon, contains at most 8, advantageously at most 5, preferably at most 4 fluorines per sulfonic functional group.

Among the impurities which can be removed by the method according to the present invention, there may also be mentioned the sulfinate ions which are often generated during the reaction for synthesizing the imide ions or which may be a product of decomposition of the imide ion. These sulfinate ions correspond to an anion which has the same empirical formula as the corresponding sulfonyl radical, to within a negative charge.

Thus, the method is perfectly suitable for the treatment of impure organic compositions of ammonium imide ion containing a sulfinate ion, in particular a sulfinate ion whose sulfur is carried by a perhalogenated carbon.

This sulfinate ion whose sulfur is carried by a perhalogenated carbon advantageously contains at most 3, preferably at most 2, perfluorinated carbons per sulfinate functional group, which functional group may also be designated by the expression "sulfinic functional group".

It is also preferable that said perhalogenated carbon carried by the sulfinic, or sulfinate, functional group contains at most 8, advantageously at most 5, preferably at most 4, fluorines per sulfinic functional group.

According to the present invention, to have separations of excellent quality, it is preferable that the number of carbons of the sulfonates present in the imide ion or imide composition as impurities, is at most equal to 12, advantageously to 6, preferably to 4.

It is preferable that the same constraint on the total number of carbons applies to the sulfinates present as impurities.

It is also preferable that the number of perhalogenated carbons of the imide ions to be purified is at least equal to that of the sulfinates or the sulfonates which may be present in said composition.

It is even preferable that the number of perhalogenated carbons of said imide ions is greater than that of the sulfinates and/or the sulfonates for the entire molecule.

It is also preferable that the perhalogenated carbons of said imide ions contain in total at least 2, preferably at least 3, fluorines more than the sulfinates and/or the sulfonates, optionally present in said composition, contain.

According to the present invention, it is preferable that said method comprises at least two steps or at least two series of steps; one of the steps or one of the series of steps being carried out by means of an aqueous phase at natural pH, that is to say whose pH is that obtained by mere contact with a substantially pure aqueous phase (spring water or tap water, or even distilled water) or at a substantially neutral pH, that is to say a pH which is regulated such that its value at the end of the exchange is within the closed interval, that is to say comprising the limits 5 to 8. This aqueous phase may be subsequently designated by $\phi_{a1}$.

The other step, or the other series of steps, of liquid-liquid exchange is carried out by an aqueous phase designated below by $\phi_{a2}$ whose pH is at least equal to 9, preferably to 10, more preferably to 11.5, in particular when a sulfonate is present in the imide or imide ion solution. Indeed, although all the acids present as impurities are superacids having an acidity close to that of the imides, in alkaline medium, very different partition coefficients are observed.

When an initial aqueous phase is used which has a pH of between 3 and 10, without buffer species (that is to say in which each species present, capable of possessing buffering power in this region, is at a concentration at most equal to $10^{-2}$, advantageously to $10^{-3}$, it is even preferable that the sum of said species satisfies this condition), in general spring water, distilled water, deionized water or water of equivalent purity, the pH is set during the bringing into contact, this pH is called natural pH. The most common conditions for bringing into contact with a neutral aqueous phase or at natural pH should be indicated. These conditions are summarized below:

temperature: between 0 and the boiling temperature of the solvent used (at the operating pressure), preferably between 10 and 30° C.;

any pressure, preferably at atmospheric pressure for reasons of ease of implementation;

mass/aqueous phase and organic phase ratio (ratio of the flow rates per unit of time in the case of continuous operations): between 0.1 and 10;

implementation by succession of mixing/decantation/drawing off batch or by continuous operation (extraction column or series of mixers-decanters);

operation by batch or continuous methodical washings (cocurrent or countercurrent).

As regards bringing into contact with a basic aqueous phase, it may be stated that the most common conditions are similar, or even identical (apart from the pH), as indicated below:

temperature: between 0° C. and the boiling temperature of the solvent used (at the operating pressure), preferably between 10 and 30° C.;

pressure (cf. above for bringing into contact with the neutral aqueous phase), preferably at atmospheric pressure;

ratio between the masses of aqueous phase and of organic phase (ratio of the flow rates per unit of time in the case of continuous operations): between 0.1 and 10;

pH: between 10 and 12.5; compromise between yield and efficacy of removal of the impurities;

implementation by one or more successions of mixing/decantation/drawing off unit operations or by continuous operation (extraction column or series of mixers-decanters).

These questions of use of common technologies are detailed below.

The liquid/liquid exchange techniques are techniques well known to a person skilled in the art which may be mixers-decanters in series and operating countercurrentwise. They can also use exchange columns.

In the case of a countercurrent implementation in mixers-decanters or in columns, with an aqueous stream playing the role of the neutral phase and of the basic phase, the phase $\phi_{a2}$ corresponds to the incoming phase and the phase $\phi_{a1}$ corresponds to the outgoing phase once the aqueous phase has passed through the series of mixer-decanters.

It is preferable that there is a solvent, this solvent may be that of the initial impure composition, it may also be a solvent which is added, and finally this may be a solvent which has been used to dissolve the imide ion and its impurities for the exchange.

The solvents which give the best results are solvents which have an atom doublet to give, it being possible for this atom to be a halogen, advantageously fluorine, a chalcogen, advantageously oxygen, or an atom of the nitrogen column.

The latter case is not preferred because this solvent has a dual use with the amines, which can make the method cumbersome. It is also preferable that the solvent is such that the atom carrying the doublet to be given is not hindered, that is to say that it does not carry more than one secondary or tertiary carbon radical.

Thus, there may be mentioned the aliphatic chlorinated derivatives such as chlorinated derivatives such as methylene chloride or trichloroethylene, these chlorinated derivatives advantageously have at least one hydrogen. There may also be mentioned the aromatic halogenated derivatives and there may also be mentioned the unhindered ethers. Thus, ethyl ether gives good results, isopropyl methyl ether also gives good results; on the other hand, diisopropyl ether gives poor results. The aromatic hydrocarbons such as benzene and toluene also give very poor results.

The main aim of the bringing into contact with the aqueous phase $\phi_{a1}$ is to remove the halides such as fluoride, chloride, or even bromide. The second step using a basic pH is designed to remove the sulfinates and the sulfonates. A single solution may be used, provided that it is sufficiently basic.

To obtain a good rate of removal of the sulfonic acids, it is preferable to be at a pH at least equal to 11.5.

During the basic washing, the quantity of base to be used is advantageously at least the quantity of base necessary to bring the aqueous phase (considered alone) to the desired pH, increased by the quantity, as equivalent, of the acid impurities salified by the organic base. This quantity is advantageously increased by a quantity ranging from 0 to 20% of the imide to be recovered, preferably from 1% to 10%, more preferably from 1 to 5%.

The recovering of the purified imide from the organic phase may be carried out in various ways. Thus, it is possible to distil the solvent and the possible excess amine in order to recover the ammonium imide after purification. It is also possible to distil on a solid or liquid base which is stronger than the amine combined with said ammonium and to thereby recover the triflimide corresponding to the base.

However, according to a preferred embodiment of the present invention, the organic phase is subjected to a basic solution (or even a suspension), that is to say whose pH is greater than 12.5, advantageously greater than 13.

Thus, the organic solution freed of these impurities may be neutralized with a relatively strong base, that is to say whose pKa is at least equal to 12.5, preferably at least equal to that of lithium hydroxide. This final neutralization makes it possible to completely release the amine corresponding to the ammonium, and to make the triflimide salt of the metal corresponding to the cation of the base. In the washing steps, it is also preferable to ensure that the quantity of base added is such that the final pH is less than 12.5. Thus, it is preferable to verify that the final aqueous purification phase ($\phi_{a2}$ in the case of two aqueous phases) has a pH which is not too basic and advantageously at most equal to 12.5.

The aqueous phase containing the imide ion may be evaporated, for example freeze-dried.

Overview of the meaning of the abbreviations used:
TFSILi: lithium bistrifluoromethanesulfonimide ($CF_3SO_2)_2NLi$
TFSI,: trialkylammonium
$NR_3$ bistrifluoromethanesulfonimide
TFSA: trifluoromethanesulfdnamide $CF_3SO_2NH_2$
TFSCl: trifluoromethanesulfonyl chloride $CF_3SO_2Cl$
TFSIH: bistrifluoromethanesulfonimide
$CF_3SO_2^-$: trifluoromethanesulfinate (triflinate, TFSH)
$CF_3SO_3^-$: trifluoromethanesulfonate (triflate, TFSOH)
DIPEA: diisopropylethylamine
$NEt_3$: triethylamine
DMAP: 4-dimethylaminopyridine By way of teaching, for example, it is possible to detail the implementation of a process sequence applied to the synthesis of lithium triflimide.

In this implementation, the method of synthesis of lithium bistrifluoromethanesulfonimide (TFSILi) comprises the following steps:
reaction of trifluoromethanesulfonyl chloride (TFSCl) with ammonia to give a mixture, here a reaction mixture, which will be taken up by the method of treatment according to the invention;
removal of the coproducts and/or of the impurities by liquid-liquid extraction according to the invention of the impure mass;
recovery of the imide ion; and optionally:
removal-recovery of the solvent;
recovery of the DIPEA by action of a base.

Preferred Operating Conditions for Optional Steps

Removal of the Solvent
pressure between 10 hectoPa and 5 bar;
the temperature is determined by the pressure;
batch or continuous;
the solvent is recovered by condensation so as to be recycled.

Recovery of the DIPEA by Action of a Base
by azeotropic distillation
pressure between 10 hectoPa and 5 bar;
temperature determined by the pressure;
base/TFSI anion molar ratio greater than 1, preferably between 1.01 and 1.2.
by decantation base/TFSI anion molar ratio at least equal to 1 and advantageously at most equal to 3/2, preferably 1.2;
temperature advantageously greater than 10° C. in order to facilitate the decantation.

The following nonlimiting examples illustrate the invention:

Exemplification of the Various Steps

The examples given below to illustrate the various steps were chosen for their demonstrative qualities. For reasons evident to a person skilled in the art, they were not all carried out on the same scale of quantities because some technologies used require large quantities for successful implementation. That does not in any way detract from the demonstration of the feasibility of the series.

Exemplification of the Reaction of the Starting Composition

EXAMPLE 1

The apparatus used comprises:
a jacketed 1 liter reactor equipped with central stirring;
a hot/cold bath which makes it possible to maintain the reaction mass at −30° C. if necessary;
a supply of ammonia gas by immersing using a 1 liter pressurized ammonia bottle;
a dry ice trap in series on a set of $N_2$ valves which make it possible to maintain the reactor at a pressure close to atmospheric pressure in the laboratory;
an injection of $CF_3SO_2Cl$ at a controlled flow rate via a propelled syringe.

The entire apparatus is placed in a ventilated hood.

Dichloromethane (490 g), DIPEA (221 g) and DMAP (3.5 g) are loaded into the 1 liter reactor.

The desired quantity of ammonia (9.7 g) is loaded by absorption at −15° C. into the dichloromethane base from the bottle by means of the plunger. The exact quantity loaded is determined by weighing and/or measuring the flow rate. The condenser, cooled with dry ice, ensures that there is no loss of ammonia outside the reactor. The solution of $CF_3SO_2Cl$ at 50% in dichloromethane (383.4 g) is then injected via a propelled syringe while the temperature of the reaction mass is maintained between −10 and −5° C.: the duration of the pouring 3 hours. The temperature is then allowed to return to room temperature (1 hour). The reaction mass is then washed with about 150 g of water so as to have two easily analyzable homogeneous phases. About 1002.7 g of organic phase and 240.3 g of aqueous phase are recovered.

The analysis of the composition of the organic and dichloromethane phases by ion chromatography gives the following results:

| Phase | Organic | Aqueous | Partition coef. $\phi_o/\phi_a$ |
|---|---|---|---|
| weight | % | % | |
| Cl— | 1.9 | 8.5 | 0.23 |
| $CF_3SO_2^-$ | 0.33 | 0.07 | 4.7 |
| $CF_3SO_3^-$ | 1.2 | 0.2 | 5.7 |
| $(CF_3SO_2)_2N^-$ | 14.8 | nd | |

These partition coefficients are scarcely favorable for the purification.

EXAMPLE 2

Example 1 is repeated, except that all the dichloromethane (680 g) is loaded into the reactor at the beginning of the operation. 268.6 g of DIPEA, 4.2 g of DMAP and 12.0 g of ammonia are then loaded. The $CF_3SO_2Cl$ (233.2 g) is then injected into the reaction medium by means of a propelled syringe. The duration of injection is 2 h 30 min during which the reaction mass is kept at −20° C. The temperature is then allowed to return to room temperature (1 hour). The reaction mass is then washed with about 300 g of water so as to have two, easily analyzable homogeneous phases. About 1040 g of organic phase and 445 g of aqueous phase are recovered.

| % by mass | Mass of the phases | $F^-$ | $Cl^-$ | $CF_3SO_2^-$ | $CF_3SO_2NH_2$ | $CF_3SO_3^-$ | $(CF_3SO_2)_2N^-$ |
|---|---|---|---|---|---|---|---|
| $\phi_o$ | 1040 g | 0 | 1.5 | 0.2 | 0.05 | 0.6 | 18 |
| $\phi_a$ | 445 g | 0 | 7.2 | 0.05 | 0.01 | 0.08 | |
| Partition coef. $\phi_o/\phi_a$ | | | 0.2 | 4 | 5 | 7.5 | |

The partition coefficients are here very unfavorable for the purification.

Exemplification of the Washes by Liquid-liquid Extraction

EXAMPLE 3

Extraction at Neutral or Natural pH

This example illustrates the way to carry out the aqueous washes to remove the chloride ions.

Example 1 is repeated, except that the ammonia is loaded at a colder temperature (−20° C.), which makes it possible to load a larger quantity of ammonia. The DIPEA, TFSCl and DMAP load is modified proportionately. The total quantity of dichloromethane loaded is unchanged. After reaction, the reaction mass is washed with 300 g of water. After decantation, the aqueous phase is removed from the reactor and 300 g of water are added. The whole is stirred for ¼ of an hour and then decantation is also allowed to proceed for ¼ of an hour. The organic and aqueous phases are analyzed by ion chromatography and then the aqueous phase is again removed. This operation is repeated four times. The variation of the composition of the different phases is illustrated in the tables below.

It is observed that the chloride ions which are troublesome for the remainder of the method and for the quality of the final product are removed from the organic phase with minimal losses of the TFSI anion whose value is to be enhanced.

| Phase | $F^-$ | $Cl^-$ | $CF_3SO_2^-$ | $CF_3SO_2NH^-$ | $CF_3SO_3^-$ | $TFSI^-$ |
|---|---|---|---|---|---|---|
| Organic phase 1st wash | 0.001 | 2 | 0.2 | 0.05 | 0.6 | 24 |
| Aqueous phase 1st wash | 0.001 | 7.4 | 0.04 | 0.05 | 0.08 | 0.05 |

-continued

| Phase | $F^-$ | $Cl^-$ | $CF_3SO_2^-$ | $CF_3SO_2NH^-$ | $CF_3SO_3^-$ | $TFSI^-$ |
|---|---|---|---|---|---|---|
| Organic phase 2nd wash | 0.001 | 0.7 | 0.2 | 0.06 | 0.6 | 26.5 |
| Aqueous phase 2nd wash | 0.001 | 3.1 | 0.06 | 0.03 | 0.09 | 0.18 |
| Organic phase 3rd wash | 0.001 | 0.2 | 0.15 | 0.03 | 0.6 | 27.5 |
| Aqueous phase 3rd wash | 0.001 | 1.2 | 0.08 | 0.015 | 0.1 | 0.06 |
| Organic phase 4th wash | 0.001 | 0.03 | 0.1 | 0.05 | 0.5 | 27.8 |
| Aqueous phase 4th wash | 0.001 | 0.3 | 0.1 | 0.017 | 0.2 | 0.1 |

| | Partition coefficient $\phi_o/\phi_a$ | | | | | | Ratio between the partition coefficient of the TFSI and that of the chemical species considered | | | | | |
|---|---|---|---|---|---|---|---|---|---|---|---|---|
| | $F^-$ | $Cl^-$ | $CF_3SO_2^-$ | $CF_3SO_2NH^-$ | $CF_3SO_3^-$ | $TFSI^-$ | $F^-$ | $Cl^-$ | $CF_3SO_2^-$ | $CF_3SO_2NH^-$ | $CF_3SO_3^-$ | $TFSI^-$ |
| 1st wash | 1 | 0.270 | 5 | 1 | 7.5 | 480 | 480 | 1776 | 96 | 480 | 64 | 1 |
| 2nd wash | 1 | 0.226 | 3.333 | 2 | 6.667 | 147.2 | 147.22 | 651.9 | 44.17 | 73.61 | 22.08 | 1 |
| 3rd wash | 1 | 0.167 | 1.875 | 2 | 6 | 458.3 | 458.33 | 2750 | 244.44 | 229.17 | 76.39 | 1 |
| 4th wash | 1 | 0.1 | 1 | 2.941 | 2.5 | 278 | 278 | 2780 | 278 | 94.52 | 111.2 | 1 |

EXAMPLE 4

This example illustrates the way to wash the reaction mass at basic pH to remove the impurities such as trifluoromethanesulfonate or trifluoromethanesulfinate.

A reaction mass having a mass of 792 g, obtained as in Example 3, that is to say washed beforehand so as to be freed of chloride ions, is placed in the 1 liter reactor described above, but equipped with a pH probe, and after having evaporated part of the dichloromethane solvent (composition organic phase 1), 300 g of water and 26 ml of 2N sodium hydroxide are added with stirring so as to obtain a pH of 10.8. Decantation is allowed to proceed for ¼ of an hour and the aqueous phase is withdrawn. 300 g of water are again added and the pH is adjusted to 10.8, with stirring, with this time 8.5 ml of 2N sodium hydroxide. After decantation, the aqueous phase is withdrawn.

The weight and the composition of the various phases are given in the tables below.

It is observed that in the organic phase 3, the content of trifluoromethanesulfonic anion and of trifluoro-methanesulfinic anion is less than 0.06% and 0.01%, respectively. This demonstrates that after three basic washes, a dichloromethane solution of the practically pure TFSIH/DIPEA complex is obtained.

|  | weight | $F^-$ | $Cl^-$ | $CF_3SO_2^-$ | $CF_3SO_2NH^-$ | $CF_3SO_3^-$ | $TFSI^-$ |
|---|---|---|---|---|---|---|---|
| Organic phase 1 | 792 | $<10^{-3}$ | 0.04 | 0.1 | 0.1 | 0.6 | 30.7 |
| Organic phase 2 | 767 | $<10^{-3}$ | 0.006 | 0.01 | 0.01 | 0.16 | 30.9 |
| Aqueous phase 2 | 342 | $<10^{-3}$ | 0.07 | 0.2 | 0.1 | 1 | 1.4 |
| Organic phase 3 | 746 | $<10^{-3}$ | 0.004 | 0.01 | 0.01 | 0.06 | 30.7 |
| Aqueous phase 3 | 321 | $<10^{-3}$ | $<10^{-3}$ | 0.02 | 0.01 | 0.2 | 1.1 |

|  | Partition coefficient $\Phi_o/\Phi_a$ | | | | | | | Ratio between the partition coefficient of the TFSI and that of the chemical species considered | | | | | |
|---|---|---|---|---|---|---|---|---|---|---|---|---|---|
|  | weight | $F^-$ | $Cl^-$ | $CF_3SO_2^-$ | $CF_3SO_2NH^-$ | $CF_3SO_3^-$ | $TFSI^-$ | $F^-$ | $Cl^-$ | $CF_3SO_2^-$ | $CF_3SO_2NH^-$ | $CF_3SO_3^-$ | $TFSI^-$ |
| $1^{st}$ wash | 2.24 | 1.00 | 0.09 | 0.05 | 0.10 | 0.16 | 22.07 | 22.07 | 257.50 | 441.43 | 220.71 | 137.95 | 1.00 |
| $2^{nd}$ wash | 2.32 | 1.00 | n.s. | 0.50 | 1.00 | 0.30 | 27.91 | 27.91 | n.s. | 55.82 | 27.91 | 93.03 | 1.00 |

The invention claimed is:

1. A method of treating an impure organic ammonium imide composition comprising bis-trifluoromethanesulfonimide and having as an impurity at least one species selected from halides, sulfonates and sulfinates, said process comprising the step of:
   a) submitting said composition to a liquid-liquid extraction by means of an aqueous phase $\Phi_a$ with a pH adjusted to a value of at least 9.

2. The method as claimed in claim 1, wherein the aqueous phase has a pH adjusted to a value at least equal to 10 or 11.5.

3. The method as claimed in claim 1, said ammonium having at least 5 and at most 12 carbon atoms.

4. The method as claimed in claim 1, wherein the ammonium carries at least two hydrocarbon-based chains, containing both carbon and hydrogen, attached to the nitrogen by a secondary carbon of $sp^3$ hybridization.

5. The method as claimed in claim 1, wherein said ammonium is a protonated amine.

6. The method as claimed in claim 5, wherein said ammonium is an alkylated protonated amine.

7. The method as claimed in claim 6, wherein said ammonium is a protonated tertiary amine.

8. The method as claimed in claim 7, wherein said ammonium is a protonated tertiary amine which cannot be quaternized.

9. The method as claimed in claim 1, wherein said impure organic ammonium imide composition contains a trifluoromethanesulphonate ion.

10. The method as claimed in claim 1, wherein said impure organic ammonium imide composition contains a trifluoromethanesulphinate ion.

11. The method as claimed in claim 1, said method further comprising submitting said composition to a liquid-liquid extraction by means of an aqueous phase $\Phi_{a1}$ at a pH between 5 and 8.

12. The method as claimed in claim 11, wherein the aqueous phase in step a) has a pH adjusted to a value at least equal to 10.

* * * * *